US008092683B2

(12) United States Patent
Carredano et al.

(10) Patent No.: US 8,092,683 B2
(45) Date of Patent: Jan. 10, 2012

(54) MULTI-MODAL ION EXCHANGE CHROMATOGRAPHY RESINS

(75) Inventors: Enrique Carredano, Uppsala (SE);
Bo-Lennart Johansson, Uppsala (SE);
Jean-Luc Maloisel, Uppsala (SE)

(73) Assignee: GE Healthcare Bio-Sciences AB, Uppsala (SE)

( * ) Notice: Subject to any disclaimer, the term of this patent is extended or adjusted under 35 U.S.C. 154(b) by 16 days.

(21) Appl. No.: 12/517,570

(22) PCT Filed: Jan. 10, 2008

(86) PCT No.: PCT/SE2008/000016
§ 371 (c)(1),
(2), (4) Date: Jun. 4, 2009

(87) PCT Pub. No.: WO2008/085116
PCT Pub. Date: Jul. 17, 2008

(65) Prior Publication Data
US 2010/0009867 A1    Jan. 14, 2010

(30) Foreign Application Priority Data
Jan. 10, 2007  (SE) ........................ 0700053

(51) Int. Cl.
*B01D 15/08* (2006.01)
(52) U.S. Cl. ............. 210/635; 210/656; 210/198.2
(58) Field of Classification Search ............. 210/635, 210/656, 659, 198.2, 502.1; 530/413, 416, 530/417
See application file for complete search history.

(56) References Cited

U.S. PATENT DOCUMENTS

| 5,834,318 | A | * | 11/1998 | Buettner | 436/518 |
|---|---|---|---|---|---|
| 6,372,425 | B1 | | 4/2002 | Arnold et al. | |
| 6,675,103 | B1 | | 1/2004 | Patterson | |
| 6,702,943 | B1 | | 3/2004 | Johansson et al. | |
| 6,794,148 | B2 | | 9/2004 | Jindal et al. | |
| 6,881,540 | B2 | * | 4/2005 | Cramer et al. | 435/6 |
| 7,144,743 | B2 | | 12/2006 | Boschetti et al. | |
| 2002/0001812 | A1 | * | 1/2002 | Smith et al. | 435/6 |
| 2002/0053545 | A1 | * | 5/2002 | Greef | 210/656 |
| 2003/0170733 | A1 | | 9/2003 | Kozmin et al. | |
| 2005/0059881 | A1 | * | 3/2005 | Balaban et al. | 600/420 |
| 2006/0096924 | A1 | * | 5/2006 | Schlueter | 210/656 |
| 2007/0095757 | A1 | * | 5/2007 | Kaplan et al. | 210/656 |
| 2007/0244307 | A1 | * | 10/2007 | Engstrand et al. | 530/417 |
| 2007/0259453 | A1 | * | 11/2007 | Engstrand et al. | 436/547 |

FOREIGN PATENT DOCUMENTS
EP    1 094 899    3/2003
(Continued)

OTHER PUBLICATIONS

Duursma, A., et al., "Synthesis and application in asymmetric C-C bond formation of solution phase ligand libraries of monodentate phosphoramidites" Org. Biomol. Chem, 2004, vol. 2, p. 1682-1684.
Galaffu, N., et al., "Polymer resin library and the discovery of highly efficient polymer supported reagents and scavengers" Molecular Diversity, 2005, vol. 9, p. 263-275.

(Continued)

*Primary Examiner* — Ernest G Therkorn

(57) ABSTRACT

The present invention relates to a method of preparing a library of resins which are useful in chromatography, which method comprises creating a diversity of multi-modal ion exchange resins; and providing the diversity in a parallel system in which each resin is presented separated from the other resin(s).

4 Claims, 8 Drawing Sheets

FOREIGN PATENT DOCUMENTS

| | | | |
|---|---|---|---|
| EP | 0 742 438 | | 6/2007 |
| WO | WO 98/53093 | | 11/1998 |
| WO | WO 01/38228 | | 5/2001 |
| WO | WO 03/024588 | | 3/2003 |
| WO | WO 2005/082483 | * | 9/2005 |

OTHER PUBLICATIONS

Johansson, B., et al., "Preparation and characterization of prototypes for multi-modal separation media aimed for capture of negatively charged biomolecules at high salt conditions" Journal of Chromatography A, 2003, vol. 1016, p. 21-33.

Johansson, B., et al., "Preparation and characterization of prototypes for multi-modal separation aimed for capture of positively charged biomolecules at high-salt conditions" Journal of Chromatography A, 2003, vol. 1016, p. 35-49.

Malmquist, G., et al., "Electrostatic calculations and quantitative protein retention models for ion exchange chromatography" Journal of Chromatography A, 2006, vol. 1115, p. 164-186.

* cited by examiner

I: 28, 29 and 30

J: 27 or 32

K: 40 or 42

L: 55 or 58

M: 51 or 53

N: 17 or 45

O: 24 or 65

MULTI-MODAL ION EXCHANGE CHROMATOGRAPHY RESINS

CROSS-REFERENCE TO RELATED APPLICATIONS

This application is a filing under 35 U.S.C. §371 and claims priority to international patent application number PCT/SE2008/000016 filed Jan. 10, 2008, published on Jul. 17, 2008, as WO 2008/085116, which claims priority to patent application number 0700053-2 filed in Sweden on Jan. 10, 2007.

FIELD OF THE INVENTION

The present invention relates to a method of preparing a library of resins which are useful in chromatography, a specific library which comprises a diversity of such resins, and to a method of using a library according to the invention to select a resin suitable for the purification of a defined substance.

BACKGROUND OF THE INVENTION

Combinatorial chemistry is one of the important new methodologies developed in the pharmaceutical, agrochemical, and biotechnology industries to reduce the time and costs associated with producing effective and competitive new drugs. Simply put, combinatorial chemistry is used to create large populations of molecules, or libraries that can be screened efficiently in large numbers for molecules having a specific bioactivity, as indicated initially by detection of binding between one or more compounds in the library with a target molecule, commonly a drug target. By producing larger, more diverse compound libraries, the probability of finding novel compounds of significant therapeutic and commercial value is increased. As with traditional drug design, combinatorial chemistry relies on organic synthesis methodologies. The difference is the scope, instead of synthesizing a single compound; combinatorial chemistry exploits automation and miniaturization to synthesize large libraries of compounds. Libraries of biopolymers may be prepared by the sequential synthesis based on randomized addition of amino acid, nucleotide, or sugar residues, or combinations thereof, to form peptides, RNAs, polysaccharides, glycosaminoglycans or the like, thereby to prepare a random mixture of oligomers. Techniques suitable for preparing protein or peptide libraries at the nucleic acid level by phage display and similar technologies also are known.

In brief, a common feature of the screening methods used in drug discovery is that they comprise a first screening, wherein widely diverse drug candidates are screened, which is followed by a subsequent screening wherein a second diversity of candidates, created based on the result of the first step, is screened.

U.S. Pat. No. 6,794,148 (Perceptive) relates to methods for screening a sample to select a ligand to a target of interest and for obtaining information about the ligand and its binding characteristics. More specifically, the disclosed methods involve combining a solution of heterogeneous ligands with the target of interest to screen the ligands on the basis of one or more binding characteristics. Ligands having the first binding characteristic bind to the target of interest thereby to form a target/ligand complex. The complex may then optionally be separated from unbound components. The complex or unbound component then is introduced to a second "dimension" capable of separating components based on a second binding characteristic. The sample solution may be obtained by the digestion of any protein, and the target may be immobilized such as on a column. Thus, in this method, the ligand diversity is provided in the solution, while the target of interest will be immobilised to a solid support. The disclosed method is useful in the preparation of pharmaceutically active compositions.

U.S. Pat. No. 6,372,425 (Merck Co. Inc.) relates to large scale affinity chromatography of macromolecules, and more specifically to a method of purifying antibodies which bind to a ligand, wherein the antibodies are present in an impure solution comprising:

(1) selecting a ligand comprising the steps of:
(a) preparing a phage expression library expressing a plurality of oligonucleotides comprising selected principle neutralization epitope (SPNE) candidate oligonucleotides;
(b) screening the phage library to determine which candidate oligonucleotide is a SPNE of the macromolecule by a process comprising attaching an essentially pure preparation of antibody to a solid-phase support and incubating the solid-phase supported antibody with the phage library to effect binding of SPNE to the solid-phase supported antibody;
(c) determining association constants and dissociation constants of SPNE-antibody interactions using surface plasmon resonance and selecting a ligand from the SPNEs identified,
(2) replicating the ligand to produce ligands;
(3) binding the ligands to a support matrix to produce bound ligands;
(4) performing column chromatography on the impure solution containing the antibodies using a chromatography column comprising the bound ligands.

Thus, liquid chromatography has been frequently used as a tool in the screening of combinatorial libraries, especially in the drug industry. However, once one specific biotechnologically produced drug candidate, such as a protein drug candidate, has been selected from the screening, there is still the substantial effort of preparing a reliable method for its manufacture. Such manufacture commonly includes the steps of genetical manipulation of a cell, such as $E.coli$; fermentation of such cells to express the protein drug; and finally an efficient purification scheme to result in a pharmaceutically acceptable purity in sufficient yields. Again, liquid chromatography is often used as one step or as a series of purification steps.

There are many well known principles of chromatography, such as affinity chromatography, wherein the biological affinity between two species is utilized, such as an antigen as the ligand which binds antibody targets, an enzyme ligand which binds target receptors etc; ion exchange chromatography, which utilize the charge attraction between a ligand and an oppositely charged target; and hydrophobic interaction chromatography, wherein hydrophobicity of ligands is utilized to interact with hydrophobic targets. A more recent chromatography principle which uses a mixture or combination of interactions is known as multimodal chromatography. For example, Johansson et al (Journal of Chromatography A, 1016 (2003) 35-49: Preparation and characterization of prototypes for multi-modal separation aimed for capture of positively charged biomolecules at high-salt conditions) disclose that aromatic multi-modal cation exchanger ligands based on carboxylic acids seem to be optimal for the capture of proteins at high salt concentrations, which is often the case when a protein is purified from a fermentation feed. A common feature of the multi-modal cation exchange ligands disclosed is that they contain hydrogen acceptor groups close to carboxylic groups. Further, Johansson et al (Journal of Chromatography A, 1016 (2003) 21-33: Preparation and characterization of prototypes for multi-modal separation aimed for capture of negatively charged biomolecules at high-salt conditions) disclose that multi-modal anion exchanger ligands based on primary and secondary amines, or both, can be equally useful for the capture of proteins at high salt concentrations. These multi-modal anion exchangers comprise hydroxyl groups in the proximity of the ionic group.

U.S. Pat. No. 7,144,743 (Ciphergen Biosystems) relates to solid substrates and to processes of making and using them in the context of separation science and analytical biochemistry. More specifically, the solid substrate is comprised of a solid support; a monocyclic or polycyclic group that is heterocyclic, heteroaromatic, or aromatic and that is substituted with a sulfate, sulfonate, phosphate, or phosphonate group; and a linking group that comprises a mercapto-, ether-, or amino-containing moiety. The linking group links the monocyclic or polycyclic group to the solid support. One advantage of the present solid substrate described herein is its high selectivity and specificity for biological substances such as immunoglobulins, together with the avoidance of costly and often detrimental cleaning processes required for prior art substrates. Two different formats are contemplated in particular. In one format, the solid support is of the form typically used for chromatography media, that is, a bead or particle. These beads or particles are derivatized with the mixed mode ligand. The beads or particles form a chromatography medium that one can use to pack the column. In another format, the solid support takes the form of a chip, that is, a solid support having a generally planar surface to which the mixed mode ligand can be attached, covalently or otherwise. In such a biochip, or microarray, format, the substrate presents a generally planar surface to which is attached a capture reagent: in the present context, a combination of a linking group and a monocyclic or polycyclic group. Thus, a biochip presents a defined region or site, more typically, a collection of defined regions or sites, on which analytes may be captured selectively. Upon capture, analytes can be detected and, optionally, characterized by a variety of techniques.

Webb et al have described combinatorial ligand libraries, see poster from abc Technologies Conference, Basle, Switzerland, 26-27 Jan. 2005: ChemSpeed Generation of Combinatorial Libraries of Chromatography Media: Application to Purification of Therapeutic Proteins (Matthew J. Webb, Jim C. Pearson, Helen R. Tatton, Ben M. Beacom & Jason R. Betley). The ligands of this library were triazine ligands, which ligands are regarded as affinity ligands i.e. ligands which are capable of binding to one biological function class of proteins only. In fact, the Webb ligands are highly specific affinity ligands, as they are capable of interacting with one subclass of proteins only.

Several more recent patents and patent applications relate to various multi-modal ion exchange ligands for use in protein purification and other separation protocols. However, there exist numerous potentially useful multi-modal ion exchange ligand structures in theory, and there is up to date no efficient and systematic way of determining which is the optimal specific structure of a multi-modal ion exchange ligand for a given target.

SUMMARY OF THE INVENTION

One aspect of the present invention is to provide a method of preparing a library of chromatography resins comprising a diverse selection of multi-modal ion exchange ligands. A specific aspect is such a method, wherein the library represents a large diversity of relatively few resins hence avoiding a subsequent screening of a huge number of resins.

A specific aspect of the invention is to utilize computer assisted design to obtain as large diversity as possible with a minimum number of candidate resins. This allows efficient screening for new selectivities, while the amount of work and associated costs are decreased.

Another aspect of the invention is to prepare a library of multi-modal ion exchange ligands, which comprises a diversity of resins wherein characteristics such as ligand structure, ligand density etc differs between the resins. The multimodal ion exchange resins may comprise multi-modal cation exchange ligands or multi-modal anion exchange ligands.

A further aspect of the invention is to provide the use of a library according to the invention in the identification and selection of at least one chromatography resin.

One or more of the aspects above may be achieved by the present invention as defined by the appended claims. Additional aspects, details and advantages of the present invention will appear from the detailed description and claims that follow.

BRIEF DESCRIPTION OF THE DRAWINGS

FIG. 4 is a score plot (PC3/PC4)for pre-processed data.

FIG. 8 shows the principle of screening a library according to the invention for different elution conditions. For a multi-modal ion exchange system, protein loading was carried out using a buffer containing 50 mM or lower counter-ion concentration. Elution was carried out in a serial step format. Each media was loaded in three different wells and each well was eluted as shown in FIG. 8.

DEFINITIONS

Figure 1:
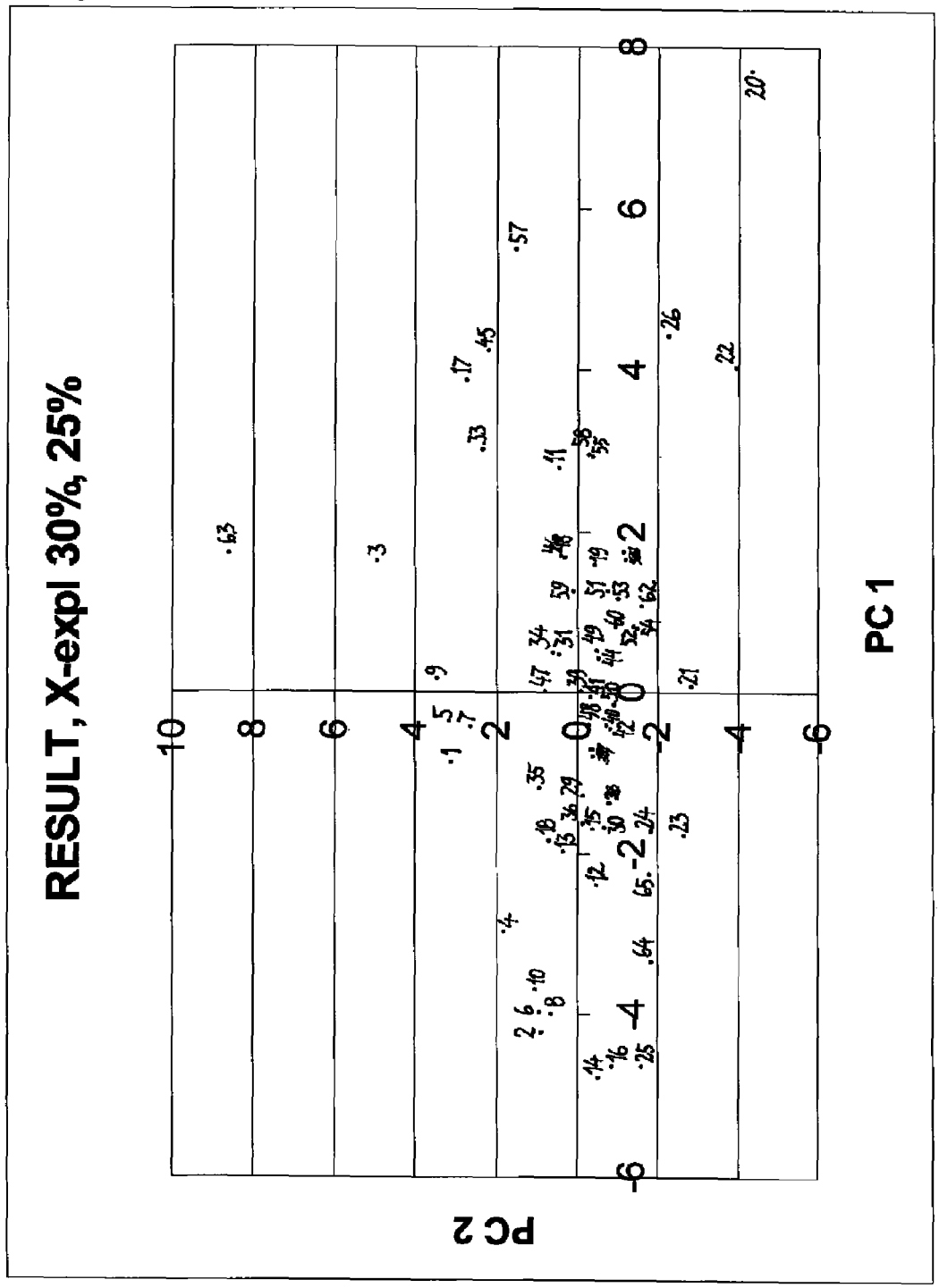
FIG. 1 is a score plot (PC1/PC2)for pre-processed data of the molecular descriptors of cation exchange ligands.

The term "multi-modal" ion exchange ligand means herein a ligand which in addition to a charged group also comprises at least one other functionality, such as a hydrophobic group, a group capable of interaction via hydrogen bonding or the like. As the term is used herein, multi-modal ion exchange ligands are known to be non-specific. Thus, the term a multi-modal ion exchange ligand means herein a multi-modal ion exchange ligand, which is capable of binding two or more different classes of proteins as defined by the well known classification of proteins according to biological function, as discussed below. In other words, as used herein, the term "non-specific multi-modal" ion exchange ligand does not include the specific kind of chromatography ligands which are known as "affinity" chromatography ligands.

The term "affinity ligand" is used in its conventional meaning within the field of chromatography, i.e. for a ligand which is capable of binding specifically to a target in a of "lock/key" kind of interaction wherein the "key" (the affinity ligand) is specific to one "lock" (a class, subclass or species of protein).

Well known examples of such specific affinity interaction are e.g. the binding of antibodies to antigens; and the binding of enzymes to receptors.

The term "protein class" as used herein refers to the classification of proteins according to biological function, as described in many handbooks in this field, see e.g. Short Course in Biochemistry by Albert Lehninger, Worth Publishers Inc. 1973 (ISBN 0-87901-024-X), Part I: Biomolecules, Table 3-4, p. 54; and Biochimie by Albert L. Lehninger (ISBN 2-257-15009-0), P. 61. In brief, the biological protein classes are Enzymes, such as ribonuclease and trypsin; Storage proteins, such as ovalbumin and ferritin; Contractile proteins, such as actin and myosin; Protective proteins of blood, such as antibodies, fibrinogen and thrombin; Toxins, such as botulinus and diphtheria; Hormones, such as insulin and somatotrophin; and Structure proteins, such as keratins and collagen.

The term "substance" means herein a single element or compound, or a mixture of elements and/or compounds.

The term resin "library" as used herein will provide a selection of different resins, wherein one or more properties such as the nature of the base matrix (natural or synthetic polymers etc); other properties of the base matrix (porosity, particle size etc); the chemical structure of the ligands attached to the base matrix; the ligand density; and/or other properties are varied.

The term "parallel" system of two or more resins means herein that the resins are used at substantially the same time and/or by the same operator, preferably in the same experiment. In an "integrated parallel" system the two or more resins are presented as physically connected to each other, such as in a format of a multiwell plate or a biochip, as compared to conventional lab bench experiments wherein the resins could be tested side by side in separate test tubes.

DETAILED DESCRIPTION OF THE INVENTION

In a first aspect, the present invention relates to a method of preparing a library of resins, which method comprises creating a diversity of resins; and providing said diversity in a parallel system in which the resins are presented separated from each other. In an advantageous embodiment, the resins are chromatography resins. Such resins may be any well known format useful in separation methods, such as particles, e.g. a chromatography gel; membranes, surfaces etc. The chromatography resins may be ion exchange resins or hydrophobic interaction chromatography (HIC) resins. In an advantageous embodiment, the resins comprise multi-modal ion exchange ligands. Multi-modal ion exchange ligands are well known and have been described. For a discussion of multi-modal cation exchange ligands and their characteristics, see e.g. Johansson et al in Journal of Chromatography A, 1016 (2003) 35-49: "Preparation and characterization of prototypes for multi-modal separation media aimed for capture of positively charged biomolecules at high-salt conditions" and EP 1 094 899. For a discussion of multi-modal anion exchange ligands and their characteristics, see e.g. Johansson et al in Journal of Chromatography A, 1016 (2003) 21-33: "Preparation and characterization of prototypes for multi-modal separation media aimed for capture of negatively charged biomolecules at high-salt conditions" and U.S. Pat. No. 6,702,943.

As is well known in this field, multi-modal ion exchange ligands are non-specific, which means that they are capable of binding two or more different biological classes of proteins. Thus, put differently, the ligands of the present library are not affinity chromatography ligands, which as well known are characterised by their ability to only bind to either one single biological class of proteins, or only to one single subclass or even species thereof.

The present resins may be multimodal in the sense that they comprise multi-modal ion exchange ligands, wherein each ligand presents functionality in addition to its charged group. However, the present invention also embraces resins which are multi-modal in the sense that they are stochastic, which means herein that they present different functionalities in such close proximity that allows interaction with the same target, such as different ligands immobilised to the same particle or carrier. Thus, instead of having the different functionalities present on the same base ligand, they can be provided on separate ligands but sufficiently close to each other to result in multi-modal binding of target. Thus, the present invention also encompasses combinations of different multi-modal ligands, and embodiments wherein the amount of the second interaction is varied in a stochastic construction. The libraries prepared according to the invention may allow two or more replicates, such as up to 10, e.g. about 5 or 6.

In this context, the term "diversity" is understood to mean that at least one property differs between the resins, also denoted descriptor. The diversity may e.g. be based on ligands having different pka, hydrophobicity, and/or number of charges. Further examples of descriptors useful in the present method are e.g. molecular weight, H-bond donor and acceptor, LogD at different pH, charge at different pH, numbers of atoms, ligand density, coupling chemistry such as the spacer coupling the ligand to the base matrix etc.

As mentioned above, in the library according to the invention, the chromatography resins are presented physically separated from each other, i.e. sufficiently separated in space to prevent any disturbing interaction between the resins, allowing independent analyses thereof. Thus, the resins may be presented in any suitable format, such as two or more parallel units e.g. chromatography columns. Such columns may be small for laboratory purposes. Thus, in an advantageous embodiment of the present invention, the resins are presented in a system of physically separated vessels, containers or compartments, preferably having walls, as compared to planar surfaces such as biochips. In an advantageous embodiment, the system is an integrated parallel system wherein the resins are part of a single format such as a multiwell plate, which is a commonly used format suitable for automated operations. In an illustrative embodiment, the plate is a 96 well plate. Each well may be of a suitable size for the experiment in question, such as 1-100 µl, e.g. 50 µl. As the skilled person will understand, it is not necessary to have different resins in each well; two or more wells may comprise the same kind of resin, provided that the herein discussed diversity of the library is obtained. Commonly, each library may comprise 16-32 resins. However, the invention also embraces methods wherein two or more resins are arranged for parallel testing, such as in chromatography columns, which testing may be manual or automated. As the skilled person will realise, the diverse resins used in the present method should be sufficiently separated from each other to allow independent testing for binding and/or elution of target molecules, such as proteins, e.g. antibodies; peptides; nucleic acids; organic molecules or the like. In an alternative, specific embodiment, the diverse resins are presented separated from each other on a substantially planar surface, such as a chip or a biochip.

In one embodiment, the present method comprises calculating two or more descriptors for the resins and then using these descriptors in conjunction with multivariate analysis to produce a multi-dimensional map for the resins. In an advantageous embodiment, the multivariate analysis is principal component analysis (PCA), which is a well known method to the skilled person in this field. Thus, the present invention may involve calculation, preferably by computer means, of two, three, four, five or more descriptors. In an illustrative embodiment, the method involves calculating four resin descriptors, and using PCA to produce a four dimensional map for the resins with the first four principal components and using the map as a guide to select resins.

In a second aspect, the present invention relates to a library which comprises a diversity of multi-modal ion exchange resins. As discussed above, such resins are well known in this field.

In a first embodiment, the present library is a diverse multimodal anion exchange resin library. The different resins may comprise any multi-modal anion exchange ligand; see e.g. the above-mentioned article by Johansson et al. The ligands may comprise amine or other positively charged groups. Functional amines can be selected from the group consisting of primary, secondary and tertiary and quaternary amines; hydrazine, such as mono-substituted hydrazine and di-substituted hydrazine; poly-amines; poly-imines; poly-Q (where Q refers to quaternary ammonium groups); aniline; and hydroxylamines. In one embodiment, stochastic resins are based on one type of amine group combined with different levels of phenyl groups, butyl groups, PEG, fluorine containing ligands and charged groups.

In another embodiment, the present library is a multimodal cation exchange resin library. The different resins may comprise any multi-modal cation exchange ligand, such as ligands comprising carboxyl or other negatively charged groups; see e.g. the above-mentioned article by Johansson et al or WO 01/38228.

In a third aspect, the invention relates to the use of a library according to the invention to select a ligand suitable for the purification of a defined target substance. As is well known, parameters which are crucial for the success of a commercial chromatography are e.g. protein capacity; protein recovery; chemical stability; and salt tolerance. The present invention allows efficient screening and selection based on one or more of these parameters. In an advantageous embodiment, the invention relates to the use of a library according to the invention is a series of screening operations, such as two or more screening operations. Such use may be to mimic a chromatographic process.

In a specific embodiment, the present invention relates to the use of a multi-modal ion exchange library; wherein a first step comprises screening a relatively large number of candidates, such as above 100; this library is limited based on the first screening results to a restricted library of about half the number of resins; this second library is screened and computer-assisted diversity evaluation is used to provide a final library comprised of a further limited number of candidates, such as 30-40 candidates. There are several commercial programs available for the present screening, such as SYBYL (7.1) and ACD/Labs. As the skilled person will understand, it is also possible to add further steps of screening in the overall process to identify an optimal chromatography resin, which process will involve initial computer-assisted steps to gather basic information; to establish suitable selection criteria; and for diversity evaluation; and one or more steps of lab work including chromatographic evaluation to assess the resin candidates. Screening parameters useful in the chromatographic evaluation include without being limiting cleaning in place (CIP), different proteins, binding capacity, pH, conductivity, elution, selectivity, organic solvents, buffers, and surfactants.

In a further aspect, the present invention relates to a method of analyzing the relative binding to at least two different multi-modal ion exchange resins of a target substance using a parallel chromatography system, which method comprises the steps of (a) providing a solution comprising the target substance;
(b) contacting, in parallel, said solution with at least two different resins;
(c) allowing target substance to bind to resins;
(d) assessing the relative binding of said at least two different resins.

In one embodiment, the parallel chromatography system comprises a multiwell plate wherein different resins are presented in different wells. In another embodiment, the parallel chromatography system comprises parallel chromatography columns.

The assessment of binding may be carried out by flow-through measurement, such as UV detection. Such methods are well known to the person skilled in the art.

The invention also comprises a method of analyzing the elution of a target substance from different multi-modal ion exchange resins using a parallel chromatography system, wherein a diversity resins are tested with respect to elution properties. Elution may e.g. be obtained by a change in conductivity by adding buffers of different salt concentrations, and/or by changing pH conditions.

Figure 8:
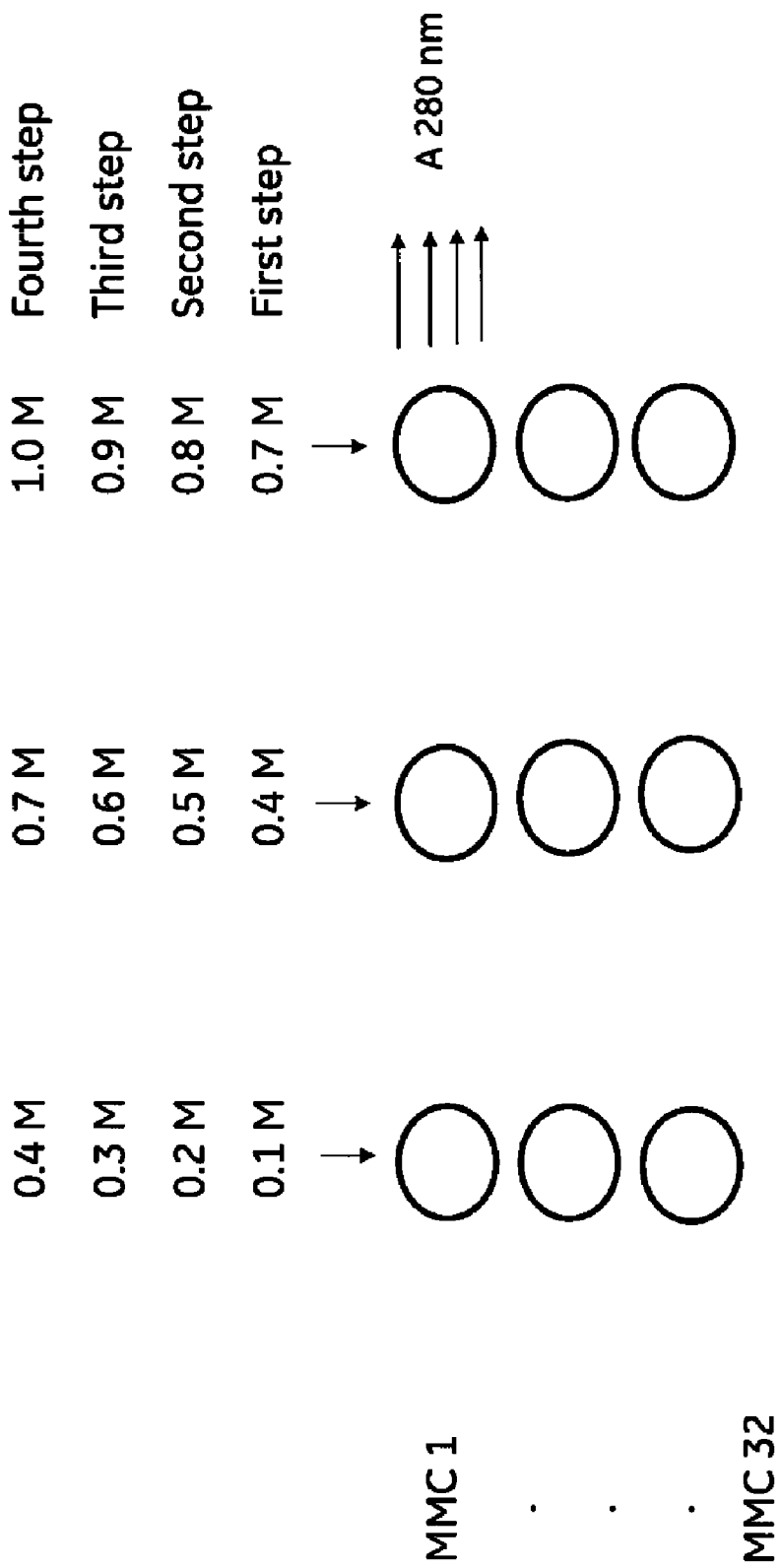
FIG. 8 shows schematically a screening approach useful in the method according to the invention.

A final aspect of the invention is a method of assessing elution conditions from chromatography resins, which method comprises providing two or more chromatography resins in a parallel system; n steps of different elution conditions for each resin in a first set of experiment; and m steps of different elution conditions for each resins in a second set of experiments; wherein there is an overlap, advantageously of one step, in the tested conditions between the first and the second set of experiments. In an advantageous embodiment, a third set of experiments follows the second set, wherein there is an overlap between the second and the third set. Each set of experiments may be comprised of any suitable number of conditions, such as 3, 4, or 5 conditions. Thus, n may be any integer between 3 and 5, and m may be any integer between 3 and 5. In an advantageous embodiment, the conditions tested are different salt concentrations, and the overlap is one salt concentration. In an advantageous embodiment, the present method comprises a third set of experiments wherein there is an overlap between the second and the third experiment. As the skilled person will understand, the method may also comprise a fourth or any number of further experiments. The principle of this aspect is illustrated in FIG. 8.

EXAMPLES

The present examples are presented herein for illustrative purposes only, and should not be constructed to limit the invention as defined by the appended claims.

Example 1

Preparation of a Diverse Library of Multi-Modal ion Exchange Resins

Method to Select a Number of Gels Comprising Multimodal Ligands for IEX

The entities described here are resins comprising multimodal ligands attached to agarose with various ligand densities. Below is disclosed a method used to select a number of entities based on enhanced diversity criteria with the purpose to reduce the number of resins to be tested. In contrast to ligand selection strategies in drug discovery, the procedure of the present invention comprises also the ligand density. Another difference is that various pH values are taken into consideration as this (the pH) is an important controlled factor in chromatographic applications. The procedure consists in calculating a number of descriptors for the entities and then using these descriptors in conjunction with principal component analysis (PCA) to produce a four dimensional map for the entities with the first four principal components. Selection is the carried out using this map as a guide (see below).

Calculation of Molecular Descriptors

There are many commercially available programs that can be used for the calculation of molecular descriptors in accordance with the invention, as these have an application of their own in drug discovery. Two examples are SYBYL (Tripos Inc) and the programs pKa and LogD from the ACD/Labs suite version 4.06. There are different ways to prepare the structure of the compounds for molecular descriptor calculation. For instance one ISIS (MDL Inc) data base was built with all the relevant structures in order to facilitate the calculations. A file in MDL format sdf was exported from the data database and imported into SYBYL. The descriptors calculated in SYBYL were calculated using the autofill function of the molecular spreadsheet and they are the molecular weight (MW), the number of hydrophobic centra (Hydrophobes) the number of H-bond donors (Donors), the number of H-bond acceptors (Acceptors) the number of rotatable bonds (Rot-Bonds), the number of atoms (AtomCount), the number of bonds (BondCount) and the number of chiral centra (Chirals). The descriptors calculated with the ACD software were the charge at pH 3, 7 and 11 using the pKa program and visual inspection of the results and the calculated partition coefficient between octanol and water (CLogD) at pH 3, 7 and 8. It was not possible to calculate CLogD for structures with quaternary nitrogen atoms for which structures the descriptor was estimated as the descriptor for a similar structure with protonated tertiary nitrogen. Finally and if the molecule was zwitterionic in nature and this was noted with a 1 if not this descriptor (zwitterion) was set to 0.

Calculation of the Descriptors for the Resins

The descriptors for the entities where calculated taking into consideration the degree of immobilisation for the ligands. For instance if ligand X with degree of immobilisation x μmol/ml was combined with ligand Y with y μmol /mL then the descriptor of the combination was given by Descriptor(X) *x/100+Descriptor(Y)*y/100.

There are many commercially available programs that can be used for the PCA analysis; for example the program 'The unscrambler' (CAMO Norway) version 9.0 was used for principal component analysis (PCA) requiring 4 components. One PCA model was created for each library excluding the objects that deviated significantly Selection of Multi-Modal Ion Exchange Ligands with PCA Analysis The data in the descriptor data set was interpreted by principal component analysis (PCA). PCA is a multivariate technique in which a number of related variables are transformed to a smaller set of uncorrelated variables. One way of looking at a principal component modal is a transformation in which many original dimensions are transformed into another coordinate system with fewer dimensions (J. E. Jackson, A users guide to principal components, John Wiley & Sons, 1991). The data were centered and scaled with $1/S_{Dev}$ before the PCA. In the score plot are objects (ligands) close to each other chemically similar and those far away from each other dissimilar. Objects far away from the origin are the extremes and the one close to origin most typical. Object/ligands close to each other in the score plot (PC1/PC2) have been grouped and the ligands in each group have been evaluated as candidates to be omitted. If the candidates from the score plot PC1/PC2 can be excluded from the library is decided from the score plot (PC3/PC4). A pair of ligands close to each other in the PC1/PC2 plot should also be situated close to each other in the PC3/PC4 plot in order to allow one of them to be excluded.

Result from the Multi-Modal Cation Exchange Library

Figure 2:
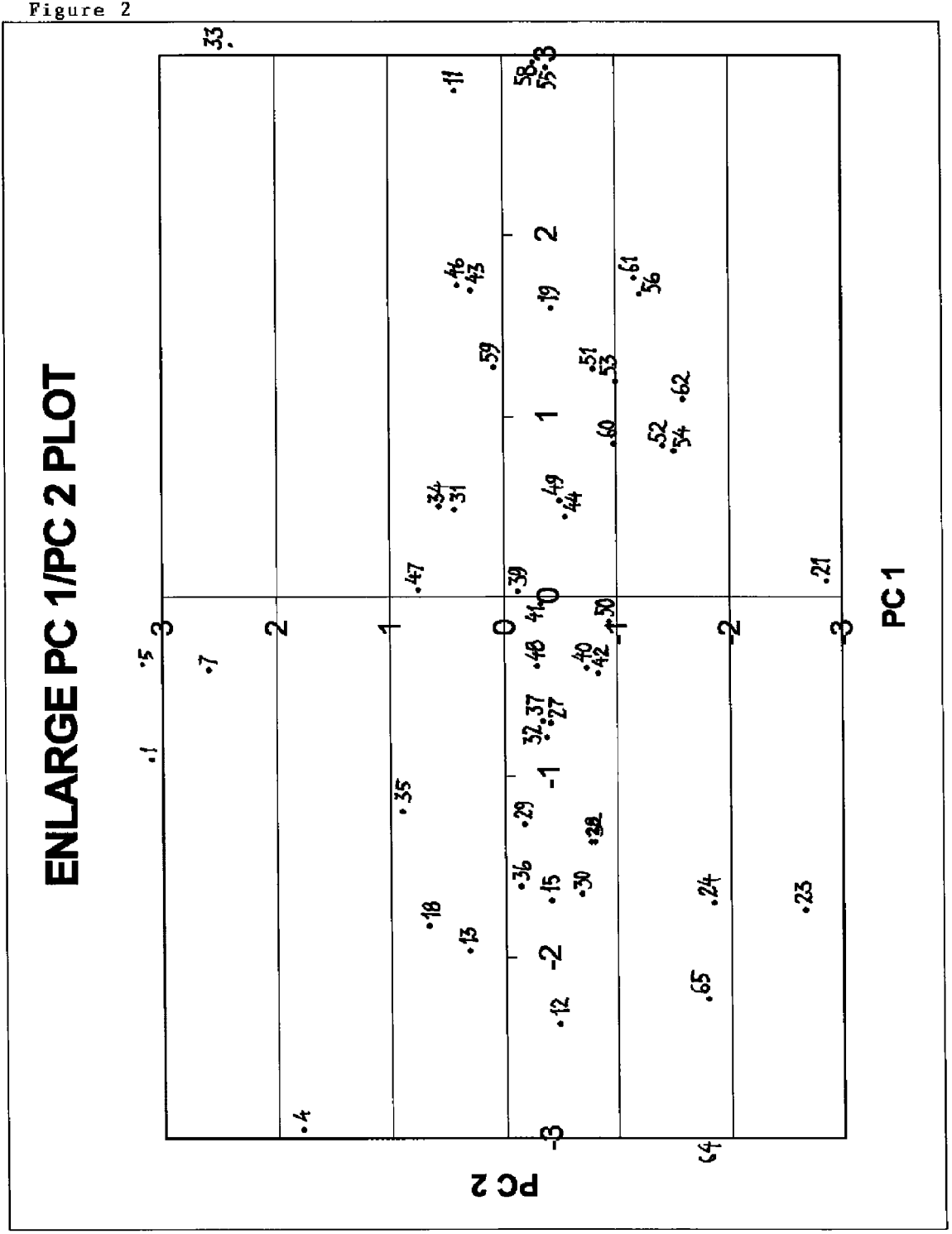
FIG. 2 is an enlarged score plot (PC1/PC2)for pre-processed of the molecular descriptors of cation exchange ligands.
Figure 3:
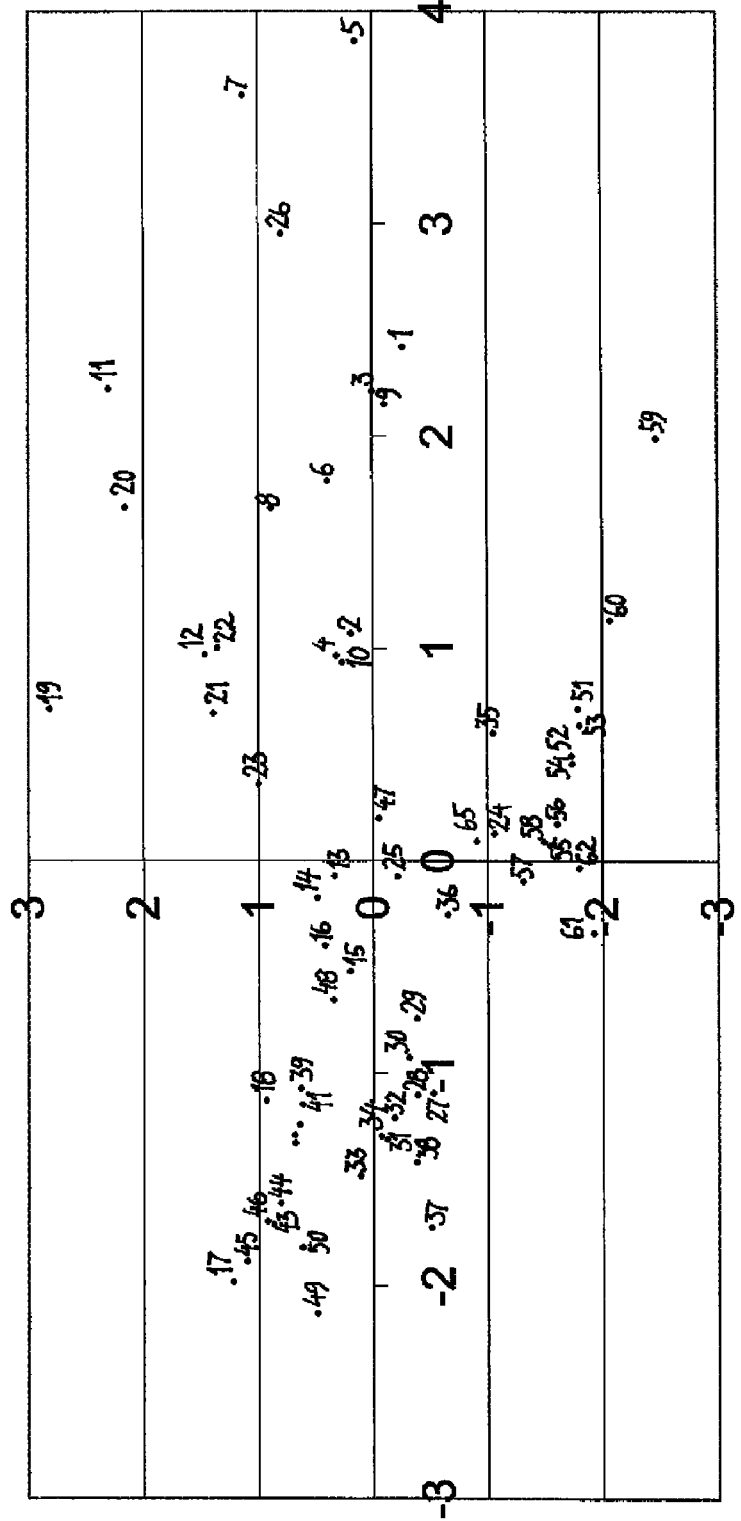
FIG. 3 is a score plot (PC3/PC4)for pre-processed data of the molecular descriptors of cation exchange ligands.
Figure 5:
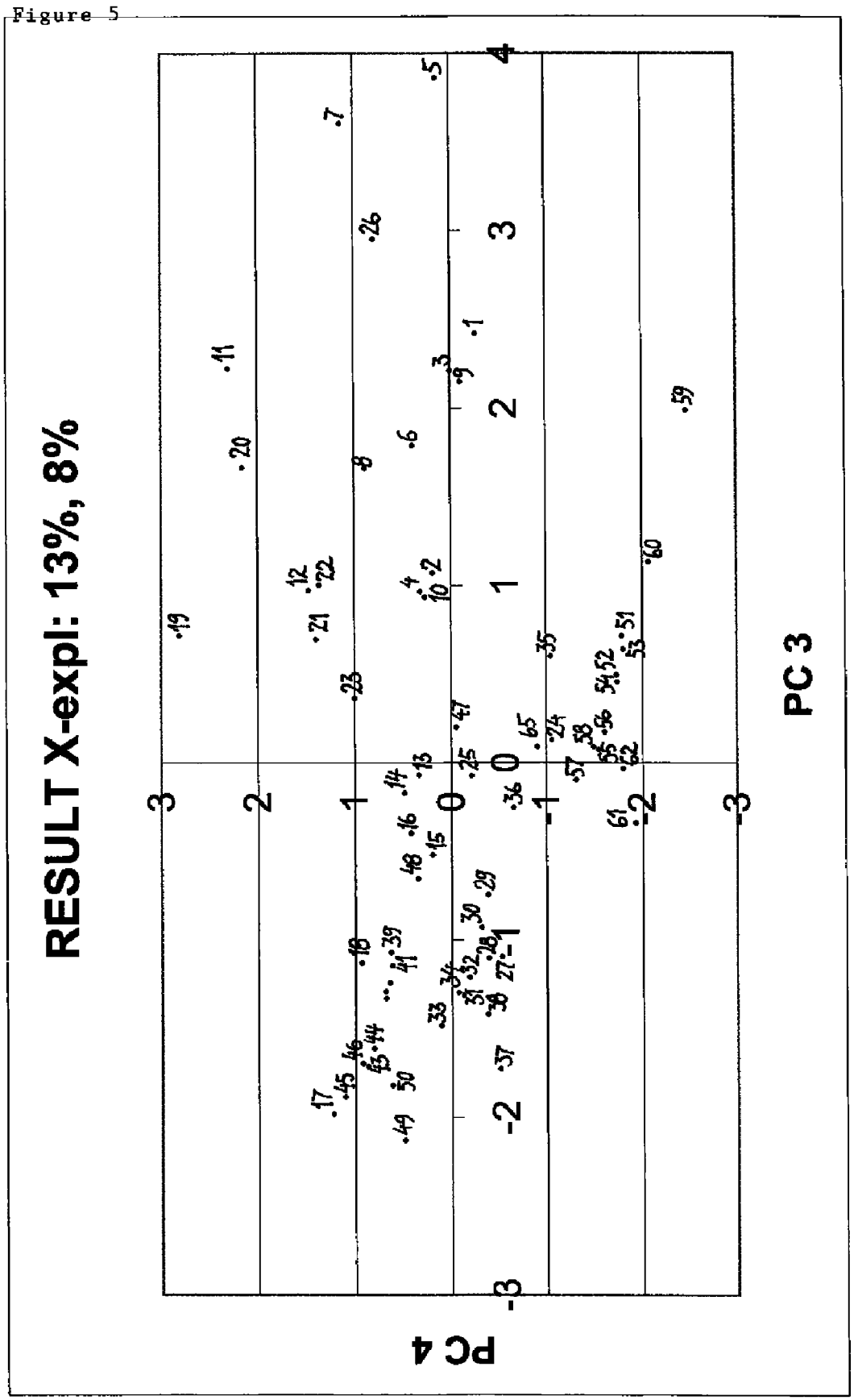
FIG. 5 shows ligand candidates for rejection after PCA analysis.
Figure 6:
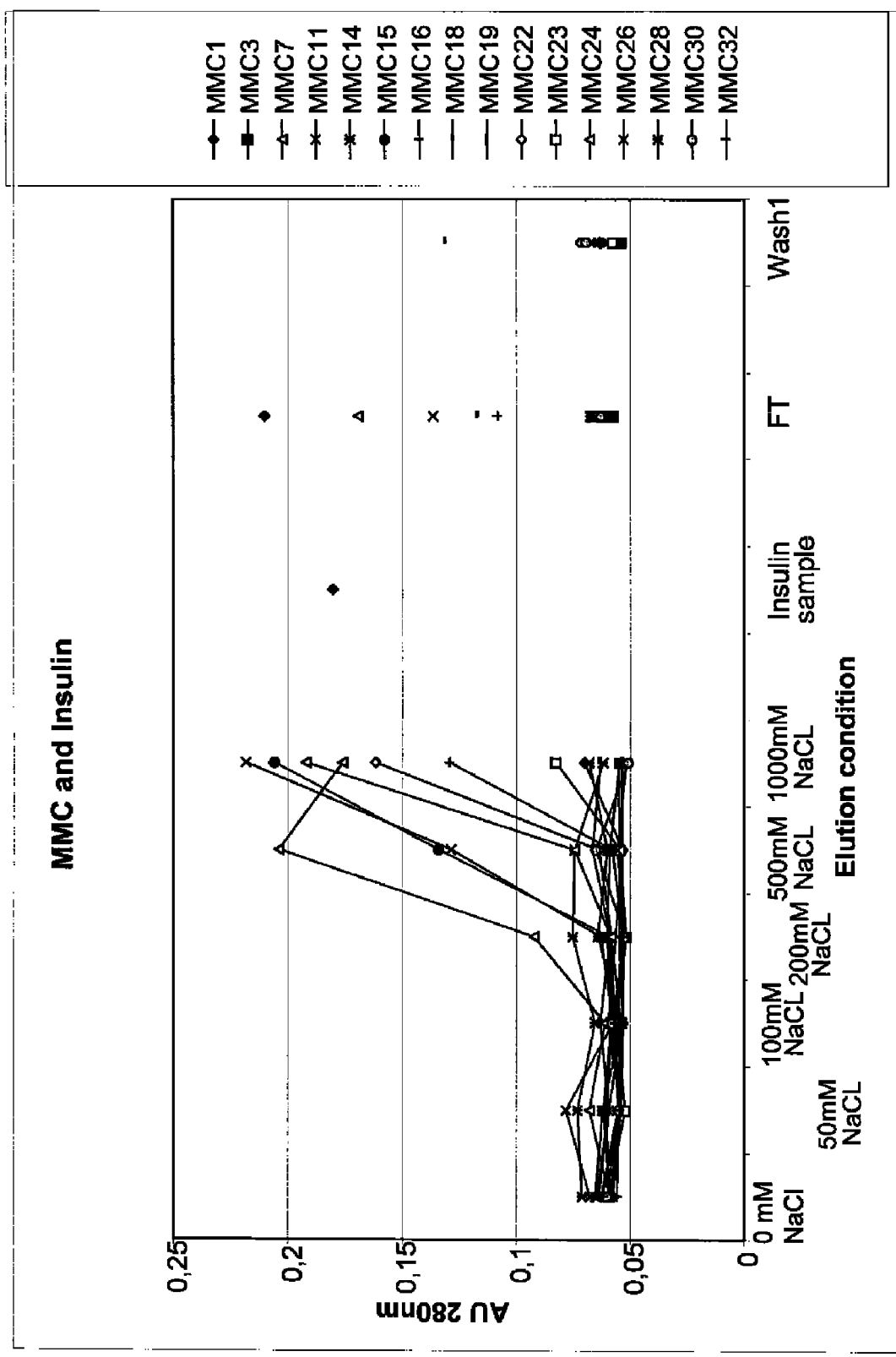
FIG. 6 shows screening as described in Example 3.
Figure 7:
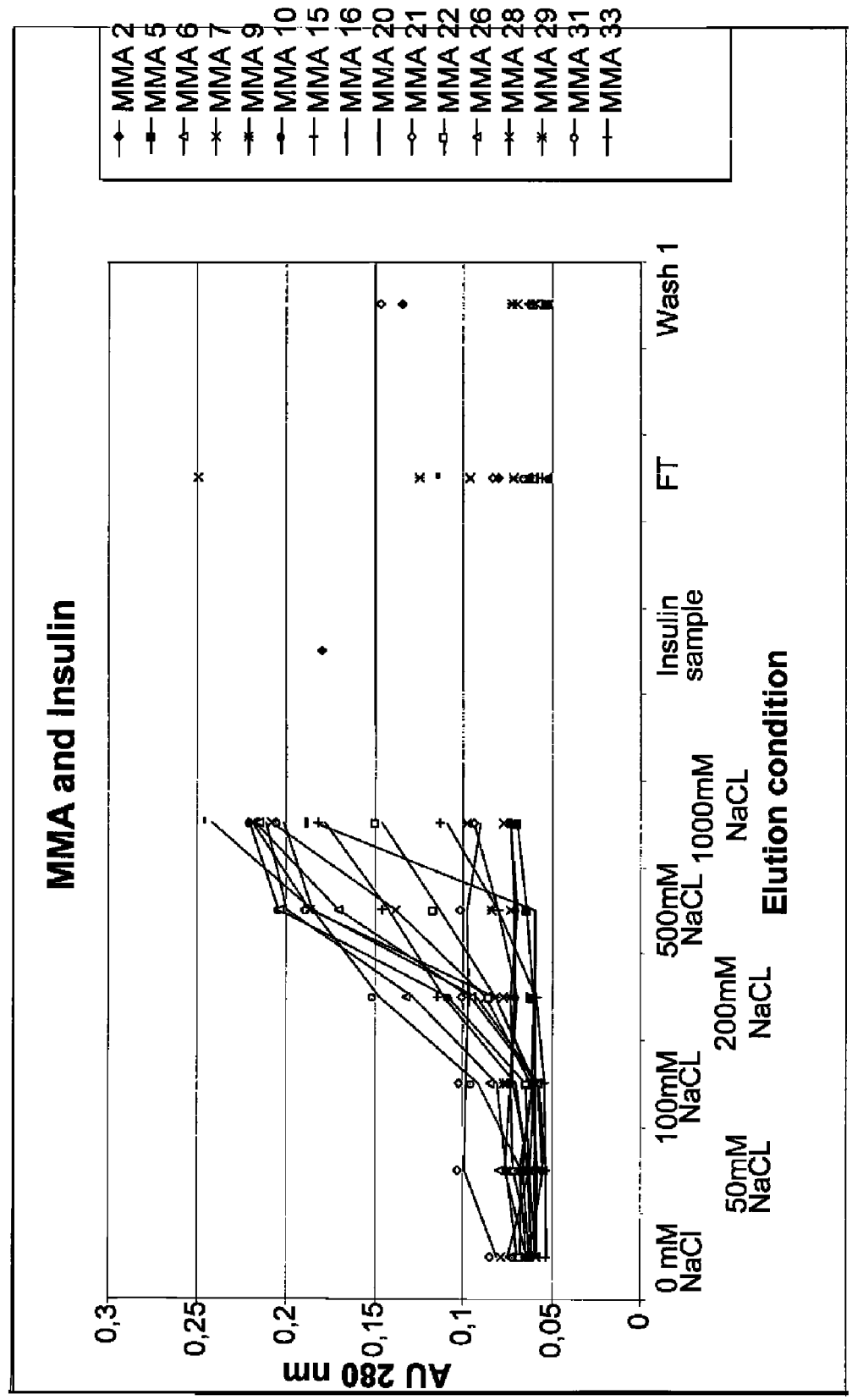
FIG. 7 shows screening as described in Example 5.

The score plot (PC1/PC2)of the molecular descriptors of a number of multi-modal cation exchange ligands is presented in FIG. 1 and FIG. 2 (enlarged plot). A number of groups (composed of ligands close to each other) have been encircled (Groups A to O in FIGS. 1 and 2). This is just an illustrative example and the size of the groups can varies. It can be noted that the score plot (PC1/PC2)explains 65% percent of the total variation in the data set. Therefore, the ligands encircled in the PC1/PC2 plot also have been marked in the PC3/PC4 plot (FIGS. 3 and 4). From the PC3/PC4 plot it can be seen that 21% of the total of the variation is explained by these principal components. This means that the four PCs explain 86% of the total variation in the data set. In this case we have decided that this is sufficient to describe the variation in the ligand properties. Therefore, the ligands situated close to each other in the two score plots (PC1/PC2 and PC3/PC4) means that one of the ligand prototypes in a par can be excluded. The ligand candidates for rejection for this example are depicted in FIG. 5.

Example 2

Preparation of a Library of Multi-Modal Cation-Exchange Resins

The library below was prepared following the principles described in example 1 above. The present microtiterplate will contain 16 prototypes (16×2 levels ×3 duplicates=96), but 24 prototypes is also possible (24×2 levels ×2 duplicates=96). As the skilled person will appreciate, in order to generate a more diverse library, some of the resins could be present with only one level of substitution so for example a scenario with 29 different ligand could be considered ((10+19×2 levels) ×2 duplicates=96).

Two lots of prototypes were based on carboxylic groups. The first carboxylic group-containing prototypes were created using homocysteine thiolactone as a scaffold. A preliminary choice was based on experience of the present inventors. Alternative structures involve groups that can present less strong binding and a potentially a facilitated elution. The prototypes are summarized below. All resins were synthesized, using standard chemistry (see e.g. WO 03/024588, Thevenin et al) with two levels of ligand substitution one around 50-60 μmol/ml and the second level around 100-120 μmol/ml.

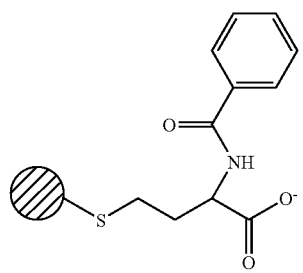

1

2

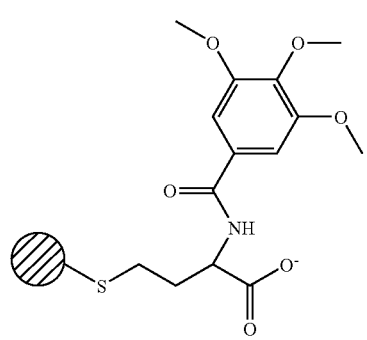

3

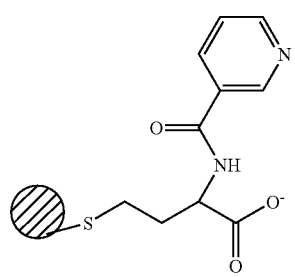

4

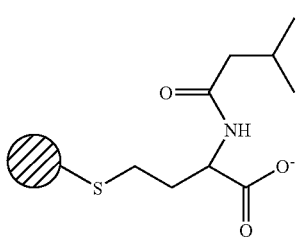

5

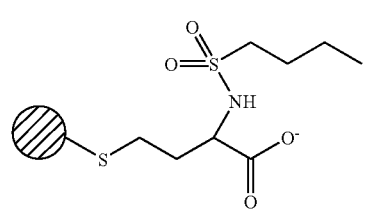

6

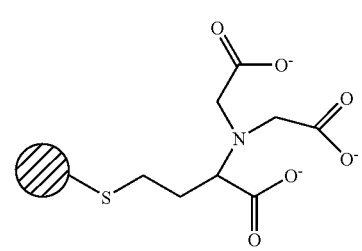

A second lot of carboxylic group-containing prototypes were based on a stochastic construction, which allowed the possibility of having different ratios between the diverse interactions in the final resin. The prototypes are summarized below.

7

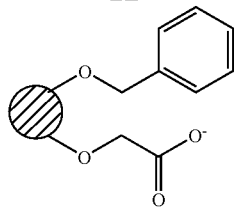

8

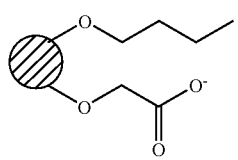

9

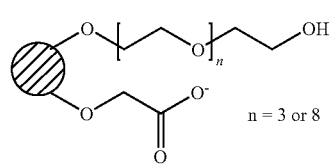

n = 3 or 8

10

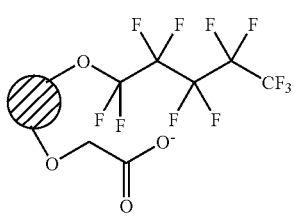

11

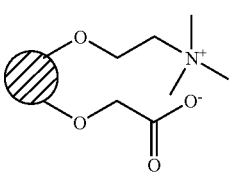

A second group of multi-modal cation exchange ligands were prototypes based on sulfonic groups as ligands, such as the ones described below.

12

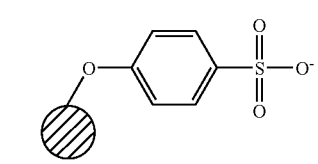

13

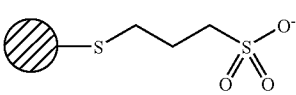

14

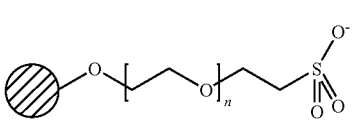

n = 4

Further multi-modal cation exchange ligand prototypes based on sulfonic groups stochastic prototypes were the following stochastic constructions:

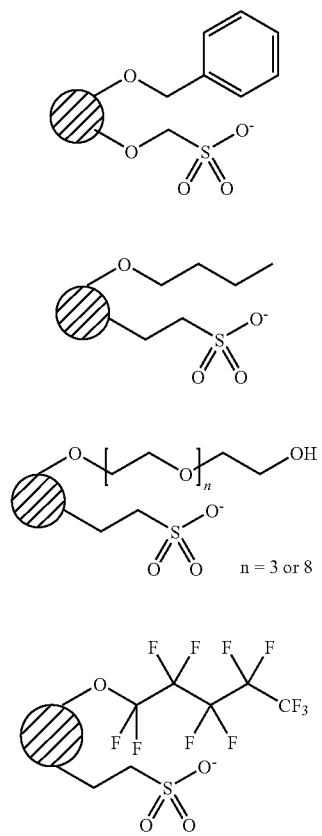

A third lot of multi-modal cation exchange ligand prototypes based on sulfonic groups were created using on surface extenders and a polymeric approach. When dextran was used as extender to attach sulfopropyl ligands to a carrier, extra binding capacity is generated.

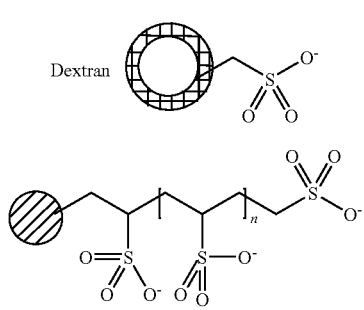

The third and last group of multi-modal cation exchange resins were based on phosphonic groups as ligands. The following are some general multi-modal structures.

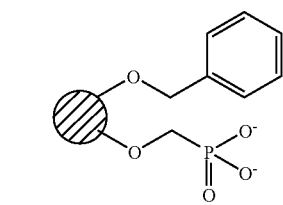

Stochastic constructions including phosphonic groups were the following.

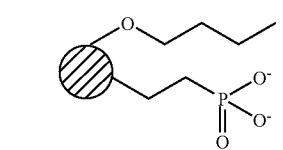

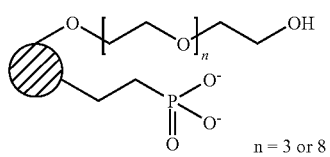

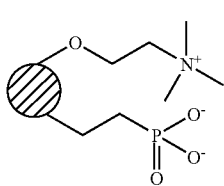

29

A third lot of multi-modal cation exchange ligand prototypes based on phosphonic groups were created using on surface extenders and a polymeric approach, as follows.

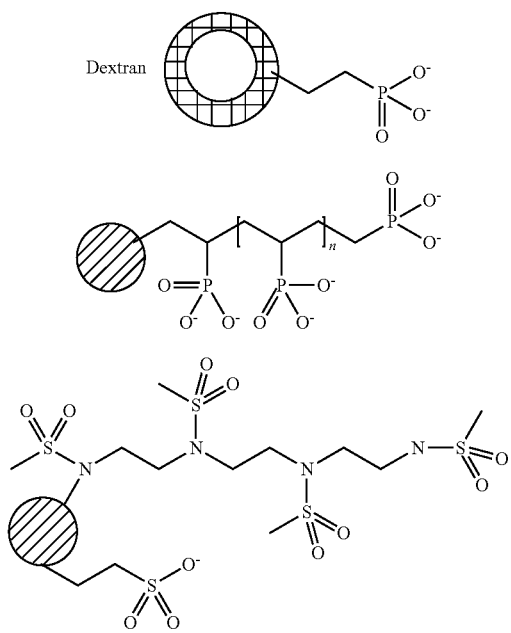

30

31

32

Example 3

Screening of Multi-Modal Cation Exchange Resin (MMC) with Protein (Insulin)

To a 96-well filter plate (a microtiter plate supplied with a filter in the bottom), 400 μl of solutions of various multi-modal cation exchange resins were applied using an automatic multi channel pump, to give a bed volume of 20 μl sedimented gel. The various gels were equilibrated with 3×200 μl of 50 mM sodium acetate pH 4.0 applied with a multi channel pipette. The solutions were forced through the bed by applying vacuum for the first to washes, and centrifugation for 1 min at 1300 rpm (approx. 350 ref) using a Beckman Coulter AVANTI® J-20XP equipped with JS-5.3 rotor for the third wash.

50 μl (0.5mg/ml) insulin (Sigma) dissolved in 50 mM sodium acetate pH 2.8 was applied to the filter plate. The resins were washed, as described above, with 3×200 μl 50 mM sodium acetate pH 4.0 and eluted with 200 μl of the following series of different salt concentrations in 50 mM sodium acetate pH 4.0: 50 mM, 100 mM, 200 mM, 500 mM and 1000 mM.

The eluate was analysed by measuring the UV-absorbance at 280 nm using a SpectraMax Plus Plate Reader.

The sample was pure insulin dissolved in 50 mM sodium acetate pH 2.8 to a concentration of 0.5 mg/ml.

Equilibration 3×200 μl 50 mM Na-acetate pH 3.2

Sample application 50 μl (0.5 mg/ml)

Wash 3×200 μl 50 mM Na-acetate pH 3.2

Elution: 100 μl elution buffer 1 200 μl 50 mM Na-acetate pH 3.2 in 50 mM NaCl 2 pH 3.2 in 100 mM NaCl 3 pH 3.2 in 200 mM NaCl 4 pH 3.2 in 500 mM NaCl 5 pH 3.2 in 1000 mM NaCl The elute was analyzed by recording the UV-adsorption at 280 nm.

In this example, there is a significant difference in selectivity between the different resins. Some of the resin prototypes e.g. MMC 16 and 18 do not seem to bind any insulin due to high absorbance in the flow through (FT). For MMC 7 and 11, it seems as if they have poor binding capacity due to high absorbance in the FT but at the same time it is possible to elute insulin from the column at least at high salt concentrations. A third group of media is the one that bind insulin irreversible e.g. MMC 3 and 30. No insulin can be detected in the FT or in the eluate.

MMC 15 and 24 seemed to be the best candidates for purifying insulin because they didn't show any loss of insulin in the FT and showed a high recovery during elution.

Example 4

Preparation of a Library of Multi-Modal Anion-Exchange Resins

The library below was prepared following the principles described in example 1 above. The list of ligands is composed of 37 different ligands and after including the ligand substitution level as a source of diversity of it results in 52 prototypes.

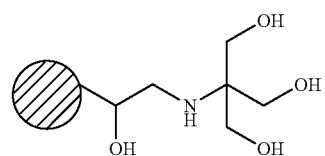

1A 200 μmol/ml
1B 100 μmol/ml

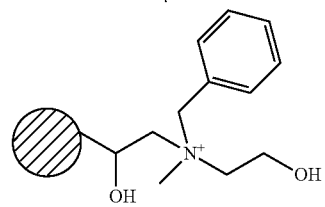

2A 100 μmol/ml
2B 60 μmol/ml

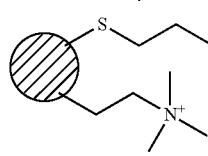
3A 200 μmol/ml
3B 100 μmol/ml
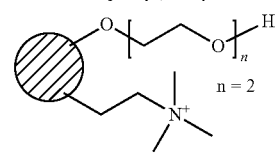
4A HS phenyl, 150 μmol/ml
4B LS phenyl, 150 μmol/ml
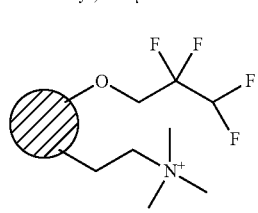
5 S-Butyl, 150 μmol/ml
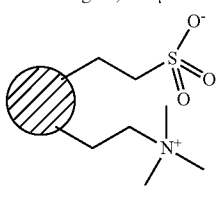
6 PEG 40 mg/ml, 150 μmol/ml
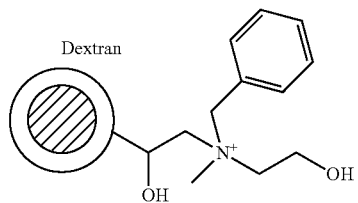
7 F 40 μmol/ml, 150 μmol/ml     8A Q 200, SP 75 μmol/ml
8B Q 200, SP 25 μmol/ml
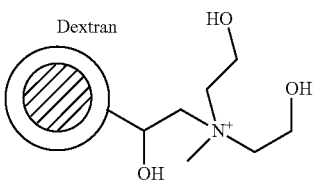
9 100 μmol/ml
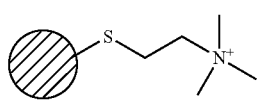
10 150 μmol/ml
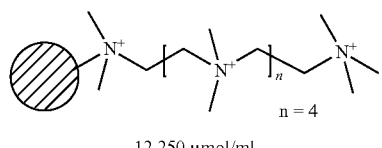
11A 250 μmol/ml
11B 150 μmol/ml
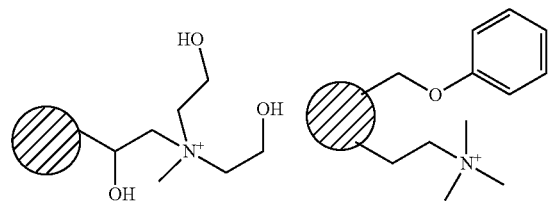
12 250 μmol/ml
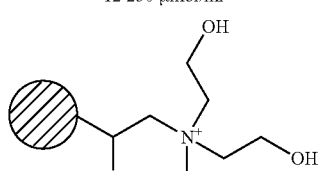
13 200 μmol/ml
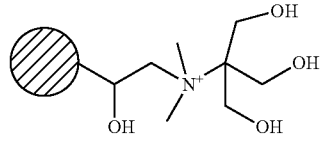
14 200 μmol/ml
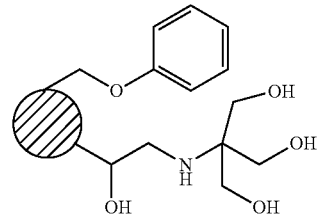
15 LS phenyl, 200 μmol/ml
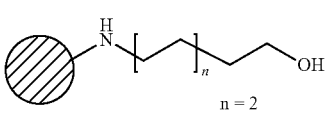
16 150 μmol/ml
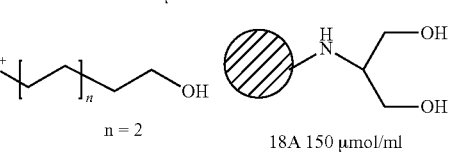 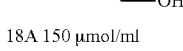  
17 150 μmol/ml      18A 150 μmol/ml
18B 250 μmol/ml
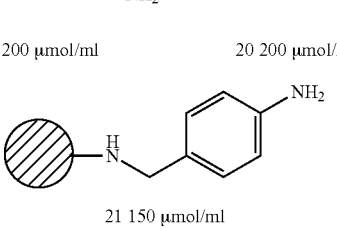 
19 200 μmol/ml      20 200 μmol/ml
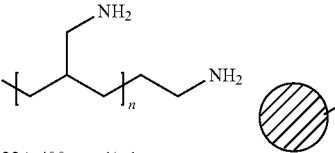
21 150 μmol/ml
 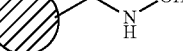
22A 400 μmol/ml     23 200 μmol/ml
22B 600 μmol/ml
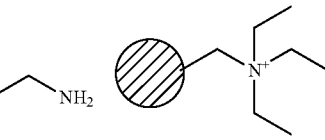 
24 200 μmol/ml      25 DEAE-Q
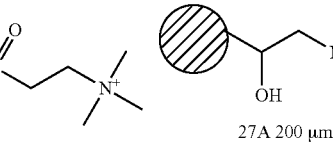 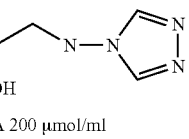 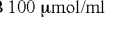
26 200 μmol/ml      27A 200 μmol/ml
27B 100 μmol/ml

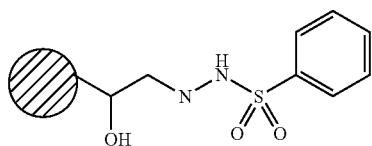

28A 150 µmol/ml
28B 70 µmol/ml

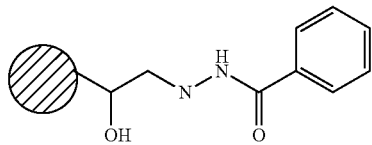

29A 150 µmol/ml
29B 70 µmol/ml

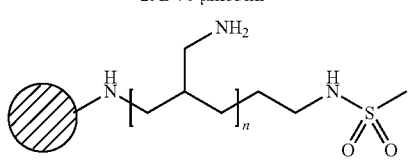

30A IC 400 µmol/ml, Sulf. 200 µmol/ml
30B IC 200 µmol/ml, Sulf. 400 µmol/ml

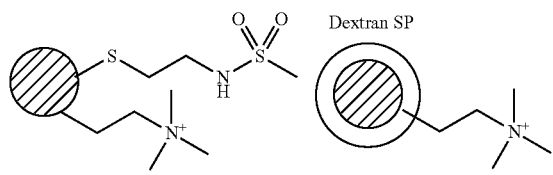
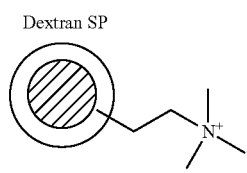

Dextran SP

31A Q 150, Sulf. 150 µmol/ml    32A Q 150, Dex. 25 µmol/ml
31B Q 150, Sulf. 300 µmol/ml    32B Q 150, Dex. 50 µmol/ml

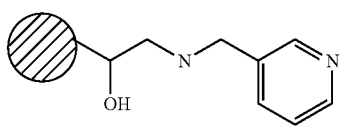

33 100 µmol/ml

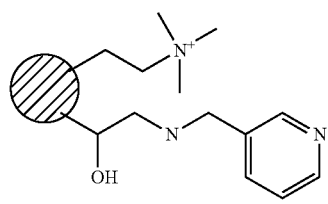

34A Q 150, Pyr. 50 µmol/ml
34B Q 150, Pyr. 100 µmol/ml

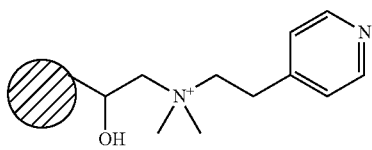

35 100 µmol/ml

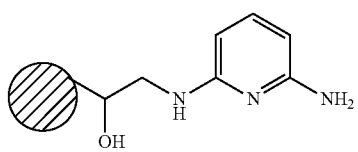

36 100 µmol/ml

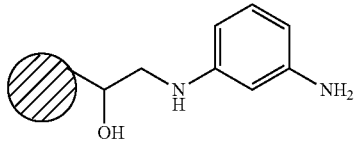

37 100 µmol/ml

Example 5

Screening of Multi-Modal Anion Exchange (MMA) Library with Protein (Insulin)

This example was basically according the procedure described above (Example 3) for the multi-modal anion exchange resins, but using multi-modal anion exchange resins and the buffers described below. A multi-modal anion exchange ligand library containing 32 candidate resins was screened using insulin as the target. The sample was pure insulin dissolved in 50 mM Tris-HCl pH 8.5 to a concentration of 0.5 mg/ml.

Equilibration 3×200 µl 50 mM Tris-HCl pH 8.5
Sample application 50 µl (0.5 mg/ml)
Wash 3×200 µl 50 mM Tris-HCl pH 8.5
Elution: 100 µl elution buffer
1 200 µl 50 mM Tris-HCl pH 8.5 in 50 mM NaCl
2 pH 8.5 in 100 mM NaCl
3 pH 8.5 in 200 mM NaCl
4 pH 8.5 in 500 mM NaCl
5 pH 8.5 in 1000 mM NaCl In this example, there is large diversity among the resins, which seem to evenly spread out judged by the absorbance for the elute fractions. There are some resins that sticks out and will be commented, with reference to FIG. 1:

MMA2 and 21 seem to be less suited candidates for the binding and elution of insulin because of their rather high abs in flow-through (FT) and wash, indicating poor binding. They also show low recovery during elution. Besides these media most of the rest seems to bind and elute insulin in a rather effective way where MMA10 seems to be slightly better than the rest.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:
1. A method of preparing a library of chromatography resins, which method comprises creating a diversity of multi-modal ion exchange resins; and
providing said diversity in a parallel system in which the resins are presented separate from each other; wherein said multimodal ion exchange resins comprise multi-modal cation exchange ligands having different pKa and wherein creating the diversity comprises calculating two or more descriptors for the resins and using the calculated descriptors in conjunction with multivariate analy- sis to produce a multi-dimensional map for the resins with the first principal components.

2. The method of claim 1, wherein the map is used as a guide to select a resin suitable for protein purification.

3. The method of claim 1, wherein the parallel system is a multiwell plate.

4. The method of claim 1, wherein the diversity further comprises a variation in at least one property selected from the group consisting of base matrix properties; coupling chemistry and ligand densities.

* * * * *